(12) United States Patent
Nielsen

(10) Patent No.: US 7,146,228 B2
(45) Date of Patent: Dec. 5, 2006

(54) SKIN ELECTRODE WITH A BY-PASS ELEMENT

(75) Inventor: Brian Nielsen, Næstved (DK)

(73) Assignee: Medicotest A/S, Olstykke (DK)

( * ) Notice: Subject to any disclaimer, the term of this patent is extended or adjusted under 35 U.S.C. 154(b) by 455 days.

(21) Appl. No.: 10/333,325

(22) PCT Filed: Jul. 11, 2001

(86) PCT No.: PCT/DK01/00483

§ 371 (c)(1),
(2), (4) Date: Jun. 26, 2003

(87) PCT Pub. No.: WO02/05712

PCT Pub. Date: Jan. 24, 2002

(65) Prior Publication Data
US 2004/0015222 A1    Jan. 22, 2004

(30) Foreign Application Priority Data
Jul. 19, 2000    (DK) ............................ 2000 01118

(51) Int. Cl.
*A61N 1/04* (2006.01)
(52) U.S. Cl. .................................. 607/142
(58) Field of Classification Search ........ 600/372, 600/386–397; 200/5 A; 607/142, 252, 153
See application file for complete search history.

(56) References Cited

U.S. PATENT DOCUMENTS

| | | | |
|---|---|---|---|
| 3,993,049 A | 11/1976 | Kater | |
| 4,180,711 A * | 12/1979 | Hirata et al. | 200/5 A |
| 4,300,575 A | 11/1981 | Wilson | |
| 4,352,359 A | 10/1982 | Larimore et al. | |
| 4,365,634 A | 12/1982 | Bare et al. | |
| 4,515,162 A | 5/1985 | Yamamoto et al. | |
| 4,539,996 A | 9/1985 | Engel | |
| 4,543,958 A * | 10/1985 | Cartmell | 600/391 |
| 4,554,924 A | 11/1985 | Engel | |
| 4,583,551 A | 4/1986 | Pike | |
| 4,674,512 A | 6/1987 | Rolf | |
| 4,757,817 A | 7/1988 | Healy | |
| 4,776,350 A | 10/1988 | Grossman et al. | |

(Continued)

FOREIGN PATENT DOCUMENTS

CA    1326063    1/1994

(Continued)

OTHER PUBLICATIONS

Pending U.S. Appl. No. 09/979,270, Steen et al., filed Nov. 21, 2001, entitled "A Skin Electrode," 24 pages.

(Continued)

*Primary Examiner*—George Manuel
(74) *Attorney, Agent, or Firm*—Sterne, Kessler, Goldstein & Fox P.L.L.C.

(57) ABSTRACT

The present invention concerns an electrode for establishing electrical contact with the skin. The electrode comprises an electrically conductive gel (12) covering a part of a first side of an electrically conductive layer (4) and an electrically conductive by-pass element (19). The by-pass element extends, on the second side of the electrically conductive layer, over the circumference of the gel on the first side and is in electrical contact with the second side of the electrically conductive layer at a point opposing an area covered with electrically conductive gel at the first side of the electrically conductive layer. The by-pass element ensures that the electrode continues to be operable even if exposed to chemical or mechanical stress.

20 Claims, 2 Drawing Sheets

U.S. PATENT DOCUMENTS

| | | | |
|---|---|---|---|
| 4,834,103 | A | 5/1989 | Heath |
| 4,838,273 | A | 6/1989 | Cartmell |
| 4,848,348 | A | 7/1989 | Craighead |
| 4,852,585 | A | 8/1989 | Heath |
| 4,895,169 | A | 1/1990 | Heath |
| 4,934,383 | A * | 6/1990 | Glumac ............ 607/152 |
| 4,989,607 | A | 2/1991 | Keusch et al. |
| 5,197,472 | A | 3/1993 | DiSabito |
| 5,203,330 | A | 4/1993 | Schaefer et al. |
| 5,250,022 | A | 10/1993 | Chien et al. |
| 5,250,023 | A | 10/1993 | Lee et al. |
| 5,264,249 | A | 11/1993 | Perrault et al. |
| 5,330,526 | A | 7/1994 | Fincke et al. |
| D366,317 | S | 1/1996 | Axelgaard |
| D423,673 | S | 4/2000 | Bassøe et al. |
| D423,674 | S | 4/2000 | Bassøe |
| D478,173 | S | 8/2003 | Nielsen |
| 6,845,272 | B1 * | 1/2005 | Thomsen et al. ............ 607/153 |
| 2003/0130714 | A1 | 7/2003 | Nielsen et al. |
| 2003/0153822 | A1 | 8/2003 | Nielsen et al. |

FOREIGN PATENT DOCUMENTS

| | | |
|---|---|---|
| DE | 27 37 665 A1 | 3/1979 |
| DK | 169235 B1 | 9/1994 |
| EP | 0 052 968 A2 | 6/1982 |
| EP | 0 322 852 A1 | 7/1989 |
| EP | 0 323 711 A1 | 7/1989 |
| EP | 0 836 864 A2 | 4/1998 |
| EP | 0 965 358 A1 | 12/1999 |
| EP | 0 985 426 A2 | 3/2000 |
| EP | 0 985 426 A3 | 3/2000 |
| FR | 2 394 873 A1 | 1/1979 |
| WO | WO 00/71024 A1 | 11/2000 |
| WO | WO 01/80943 A1 | 11/2001 |
| WO | WO 01/91637 A1 | 12/2001 |
| WO | WO 02/05712 A1 | 1/2002 |
| WO | WO 02/07597 A1 | 1/2002 |

OTHER PUBLICATIONS

Pending claims from U.S. Appl. No. 09/979,270, Steen et al., filed Nov. 21, 2001 as amended Mar. 19, 2003, 3 pages.

Pending claims from U.S. Appl. No. 10/258,807, Nielsen et al., filed Oct. 28, 2002, as amended Oct. 28, 2002, 3 pages.

Pending claims from U.S. Appl. No. 10/296,708, Nielsen et al., filed Nov. 27, 2002, as amended Nov. 27, 2002, 5 pages.

Pending U.S. Appl. No. 10/333,780, Bassoe et al., filed Jan. 24, 2003, entitled "An Electromedical Electrode with a Snap Connecting Means," 20 pages.

Pending claims from U.S. Appl. No. 10/333,780, Bassoe et al., filed Jan. 24, 2003, as amended Jan. 24, 2003, 4 pages.

English Language Translation of French Patent Publication No. FR 2 394 873, Internationalt Patent-Bureau, Jan. 4, 2002, 15 pages.

Dialog File 351, Accession No. 1979-C0411B, Derwent WPI English language abstract for German Patent Publication No. DE 27 37 665, Derwent Information Ltd.

* cited by examiner

SKIN ELECTRODE WITH A BY-PASS ELEMENT

CROSS-REFERENCE TO RELATED APPLICATIONS

This application is the § 371 U.S. National Phase Entry of International application No. PCT/DK01/00483, filed Jul. 11, 2001 and published under PCT Article 21(2) in English, which is incorporated herein by reference.

INTRODUCTION

The present invention relates to an electrode for establishing electrical contact with skin. More specifically, this invention relates to a physiological electrode whereby one or more physiological functions may be monitored or stimulated.

TECHNICAL BACKGROUND

Electrodes establishing electrical contact with the skin are used for the supplying electrical signals to the body as well as measuring electrical signals generated in or by the body.

Electrical signals may be supplied to the body of a patient through skin electrodes for various purposes, including the treatment of fibrillation by administering an electric shock, pain relief, and promotion of healing. The electric shock counteracts atrial or ventricular fibrillation of the heart, and, if the treatment is successful, makes the rhythm of the heart revert to the normal mode.

Electric signals generated in the body may be measured by skin electrodes and monitored on a suitable monitoring device. In particular, the electrical signals of the heart may be monitored on a electrocardiogram (ECG) to monitor the function of the heart.

Skin electrodes should meet a plurality of requirements to be suitable for supplying or measuring electrical signals, e.g. the skin electrodes must be sufficiently flexible to conform with the patient's body to secure a sufficient contact area, and to display satisfactory adhesion and electrical contact with the patient's body when the electrodes are placed properly.

A special requirement for a physiological electrode is that the electrode should withstand chemical and mechanical stress without deterioration. As electrodes are frequently a part of the standard emergency equipment used by rescue teams and in remote areas, the reliability of the electrodes may be crucial for saving lives. Furthermore, in the absence of a stabile and reliable electrode, the emergency equipment should be constantly controlled and old not used electrodes must be disposed of.

The electrically conductive layer of the physiological electrode may deteriorate during storing, handling or use resulting in a poor or absent electrical contact between the central area thereof and a wire connecting the electrode with an apparatus supplying or measuring electrical signals.

In EP 0 965 358 it is suggested to connect the electrically conductive layer with a sacrificial electrode prepared of a material more sensitive to corrosion than the material selected for the electrically conductive layer. While stored, the electrically conductive layer will remain unaffected, whereas the sacrificial electrode will deteriorate. While the use of a sacrificial electrode to a certain extent may protect the electrode from deterioration due to chemical attack, the electrode cannot operate satisfactory if the electrically conductive layer is broken.

In one aspect, the present invention aims at providing an electrode having the ability to withstand the chemical and/or mechanical stress which may occur during storage, handling and/or use. Especially, in a certain aspect of the invention, it is desired to provide an operable electrode having an electrically conductive layer exposed to corrosion.

DISCLOSURE OF THE INVENTION

The invention concerns an electrode for establishing electrical contact with the skin, comprising an electrically conductive layer provided with means for establishing electrical connection to an apparatus for supplying or measuring electrical signals, and an electrically conductive gel covering a part of a first side of the electrically conductive layer so that the circumference of the electrically conductive gel at least partly crosses the surface of the first side of the electrically conductive layer, wherein an electrically conductive by-pass element, provided with means for establishing electrical connection to said apparatus for supplying or measuring electrically signals, on the second side of the electrically conductive layer, is provided so that it extends over at least a part of said second side opposing the circumference of the gel crossing the surface of the electrically conductive layer on the first side and is in electrical contact with the second side of the electrically conductive layer at at least one point opposing an area covered with the electrically conductive gel at the first side of the electrically conductive layer.

Usually, the electrically conductive gel is contained in a frame. At the interface between the gel and the frame, deterioration of the edges of the electrically conductive layer is often observed for electrodes stored for a prolonged time. Furthermore, a rupture of the electrically conductive layer in the area surrounding the interface closest to the connector may occur resulting in the absence of electrical contact between the middle of the electrically conductive layer and the connector.

The reason for this deterioration or rupture is not fully understood, however, it is believed that oxygen migrates through the frame and comes into contact with the electrically conductive gel. This contact results in a reaction creating acidic or alkaline compounds able to cause corrosion of the electrically conductive layer.

The rupture of the electrically conductive layer may also be caused by mechanical stress. For example, during use of the electrode, the connector to the apparatus supplying or measuring the electrical signals can be stressed to such an extent that the electrically conductive layer deteriorates or even breaks.

The by-pass element will conduct the current from a non-corroded part of the electrically conductive layer to the connector whether or not the electrically conductive layer is conducting the electrical current. Thus, in a case where the electrically conductive layer is ruptured, the electrode will still operate satisfactory.

The by-pass element and the electrically conductive layer may be prepared of the same or a different material. The material for the by-pass element and/or the electrically conductive layer may be any suitable material which can conduct the electric current satisfactory. For example, the electrically conductive layer and/or the by-pass element may be a metallic layer comprising tin, aluminium, zinc, lead, or any alloy comprising said metals. The metallic layer may be covered on the side facing the intervening part with an agent which improves one or more of the electrical characteristics. Suitably, the metallic layer may be covered with a salt of a metal contained in the metallic layer. As an example, an electrically conductive layer comprising tin may be covered with stannous chloride to improve the conductivity when contacted with the electrically conductive gel.

Alternatively, the electrically conductive layer and/or the by-pass element may be a conductive ink printed on a suitable insulating carrier. The conducting material in the ink may be carbon particles, metal particles and/or particle of a metal salt. In a preferred embodiment, the ink comprises a suitable binding agent and particles of a metal and a salt of said metal. The metal may e.g. be tin, aluminium, zinc, lead, or silver. Silver is preferred due to its good conductive properties. The anion of the particles of the metal salt may e.g. be chloride, bromide, or iodide. In one aspect of the invention, the electrically conductive layer and/or the by-pass element comprises Ag and AgCl particles distributed in the binding agent. The carrier for the conducting ink may be any suitable insulating material. Preferably, the carrier for the conducting ink is a polymeric material, such as polyethylene, polypropylene, polyvinylchloride, polyesters, polyamides, and polyurethanes.

The by-pass element is designed to extend over at least a part of a side of the electrically conductive layer opposing the circumference of the electrically conductive gel crossing the surface of the electrically conductive layer on the other side. Preferably, the by-pass element extends to a central area of the electrically conductive layer to ensure that current can be conducted even if large areas around the circumference of the electrically conductive layer is corroded. At at least one point of a side of the electrically conductive layer opposing an area covered with the electrically conductive gel on the other side, an electrical contact is provided. The electrical contact may be provided by any suitable means, such as soldering, welding, rivetting or simple physical contact.

In a first embodiment, a shield is provided between the by-pass element and an area of a side of the electrically conductive layer opposite to at least a part of the circumference of the electrically conductive gel on the other side. The shield is suitably of a material which does not corrode at the environmental conditions existing inside the electrode. Also, it is preferred that the shield is flexible and supportive so that mechanical stress exerted on the electrode does not result in a rupture of the by-pass electrode. A suitable material for the shield is an insulating polymeric material, such as an insulating adhesive tape.

In another embodiment of the invention, the shield is omitted. In this embodiment of the invention, it is preferred to use a flexible, non-corroding carrier covered with a conductive ink as the by-pass element.

The electrically conductive layer and the by-pass element are both provided with means for connecting to an apparatus for supplying or measuring electrical signals. Whereas the connection means may be separate, it is preferred that the by-pass element and the electrically conductive layer have common means for connection to the apparatus.

The by-pass element and the electrically conductive layer may be attached to the means for connection the apparatus at a connector zone of the electrode by suitable means, such as soldering, rivetting, welding or simple physical contact. Suitably, the means for connection to the apparatus is placed off-centre near the circumference of the electrode to avoid or decrease a possible contribution to the electrical signal from the wires and the movement thereof. The means for connection to the apparatus is e.g. a suitable connector adapted to mate a corresponding plug provided in an end of an electrical wire, which, in the other end, is connected to the apparatus. The wire may also be physical attached to the electrode by soldering etc. or the wire may be provided with a suitable clip for electrical connection to the electrode.

It is, however, preferred that the by-pass element and the electrically conductive layer are releasably connected to the wire. The releaseable connection allows the electrode to be designed as a disposable article. Thus, the electrode may be adapted for single-use and may be disposed of in any suitable way.

The electrically conductive gel covers a part of a side of the electrically conductive layer so that at least a part of the circumference of the gel crosses the surface of the electrically conductive layer. The circumference of the electrically conductive gel may be entirely surrounded by the electrically conductive layer, e.g. centred provided on the electrically conductive layer. Alternatively, the electrically conductive gel can be provided so that a part thereof extends beyond the circumference of the electrically conductive layer. As the electrically conductive layer tends to corrode at an area in the vicinity of the circumference of the electrically conductive gel, it is material for the invention that the by-pass element, on the other side of the electrically conductive layer, is provided so that it extents over such area. When the electrode is provided with a connector placed near the circumference, the by-pass element preferably extends from the connector zone over said area to a part of the electrically conductive layer which is less prone to corrosion.

Various electrically conductive gels well-known to a person skilled in the art may be used in the electrode according to the invention. Preferred gels are prepared of hydrophilic polymers. In the following, gels prepared of hydrophilic polymers will be termed hydrogels. Hydrogels comprise an amount of water which improves the skin compatibility and lowers the electrical resistance.

The hydrophilic polymer may for instance be selected from the group consisting of polyacrylate, polymethacrylate, polyacrylamide, poly(vinyl alcohol), poly(ethylene oxide), poly(ethylene imine), carboxymethylcellulose, methyl cellulose, poly(acryl amide sulphonic acid), polyacrylonitril, poly(vinyl-pyrrolidone), agar, dextran, dextrin, carrageenan, xanthan and guar.

The electrically conductive gel is preferably a flexible stiff gel which maintains the integrity during storage and applications. However, the electrically conductive gel may be in the form of a viscous paste or creme, if so desired.

The pH of the electrically conductive gel may have any suitable value, i.e. the gel may be acidic, neutral, or alkaline. In one aspect of the present invention, the electrically conductive gel provides for an acidic or an alkaline corrosion of the electrically conductive layer. The acid or alkaline electrically conductive gel, respectively, may be provided in any suitable way. In one embodiment, a mineral or organic acid or base providing for the eventually obtained pH, is added to the gel during the preparation thereof. Examples of mineral or organic acids applicable are hydrochloric acid, sulphuric acid, nitric acid, phosphorus acid, acetic acid, formic acid, benzoic acid, and sulfonic acid. Examples of mineral or organic alkaline substances that may be used are ammonia, potassium hydroxide, sodium hydroxide, calcium hydroxide, pyridine, and aniline. In another embodiment explained in more detail below, the polymers of the hydrogel structure itself contain acid or alkaline groups. In a third embodiment of the invention, a combination of the two preceding embodiments is used, i.e. the gel contains a mineral or organic acid or base added during the preparation as well as polymers carrying acid or alkaline groups.

If the corrosion of the metallic layer is performed in an acidic environment, it is preferred that the polymer comprises acid groups, such as carboxylic, sulphonic, or nitric groups. In acidic environments, such groups will predominantly be anionic and may thus be capable of transferring a cation carrying a charge between the skin of the patient and the metallic layer. A preferred polymer is polyacrylate or polymethacrylate, or a copolymer containing acrylic acid or methacrylic acid as one of its monomers.

A polyacrylate having a low pH may contain a fairly large amount of water providing a sticky gel capable of penetrating the small pores of the skin. In a preferred embodiment of the invention, the content of water in the hydrogel is above 50% by weight, more preferred above 70% by weight, if the pH of the gel is between 1 and 3. The satisfactory coupling between the gel and the surface of the skin of a patient results in a low skin impedance. The satisfactory coupling also ensures a high energy transfer resulting in substantially no burning of the skin. Furthermore, the electrode adheres well to the skin of the patient and remains in position during operation, even if tension is applied thereto.

If the corrosion of the metallic layer is provided in an alkaline environment, it is preferred that the ionizable groups of the polymeric structure are basic groups, such as amine, imine, or amide groups. In alkaline environments, such groups will predominantly be cationic and thus capable of carrying a free anion in the gel.

Preferably, the gel provides an acidic corrosion of the metallic layer. The pH of the electrically conductive gel may be chosen in consideration of the selected metallic layer and may be determined by a person skilled in the art through routine experiments.

If an acidic electrically conductive gel is used, the pH may be between 0 and 4, or preferably between 1 and 3. The pH value is selected as a trade-off between skin compatibility and sufficient corrosion of the metallic layer. Therefore, preferred metals for the electrically conductive metallic layer is to be selected from metals having a high sensitivity to acid or base. Preferred metals include tin, aluminium, zinc, and lead, and any combination thereof. Tin is the most preferred metal for the metallic layer. The purity of the used metal is usually high, preferably 99% by weight or more. The thickness of the metallic layer is not of particular importance to the present invention. A thickness of 0.05 mm has proved to be reasonable.

In order to be electrically conductive, the hydrogel contains electrolytes, which carry the electrical charges. However, the presence of electrolytes also increases the tendency of the electrically conductive gel to be aggressive to the electrically conductive layer even though the pH of the hydrogel is close to the neutral pH area. This tendency is attenuated if the gel is acidic or alkaline.

Even though some ions may be etched from the metallic layer and serve to transfer an electrical charge between the metallic layer and the skin surface, it may be desired to add further ions to the gel to improve the conductivity. The ions may be added as an ionizable salt. In principle, any ions having the ability to move in the gel are applicable. However, referred ionizable salts are KCl, KBr, NaCl, AgCl or $SnCl_2$.

In one aspect of the present invention it pertains to an electrode in which an electrically conductive gel is used, wherein the pH of the gel is chosen so as to provide for a corrosion of the electrically conductive layer. Without intending to limit the scope of the invention to a specific explanation or theory, it is presently believed that the chemical attack of the metallic layer provides a diminished impedance at the interface between the metallic layer and the acidic gel. The chemical attack will result in the creation of pits in the surface of the metallic layer, thus increasing the surface area so that the electrical contact between the gel and the metallic layer is improved. It is also believed that the generation of a relatively high concentration of metallic ions at the interface contributes to the availability of current carriers when a current is applied, resulting in a reduced tendency to build-up charge, i.e. to serve as a capacitor.

Whereas the electrically conductive gel used in the present invention is preferably a hydrogel having the ability to adhere to the skin of the patient, it may be preferred to cover the face opposing the face in contact with the electrically conductive layer by a second or further electrically conductive skin adhering layer(s) having a pH more compatible with the skin of the patient. The pH of the second gel layer is preferably 5–9.

During storage, the surface of the electrically conductive intended to adhere to the skin is suitably provided with a liner. Immediately before use, the liner is removed and the electrode is attached to the skin of a subject.

The electrode according to the invention may be stored in any suitable container. Preferably, the container consists of a material which substantially impedes or prevents permeation of gases. In a preferred embodiment, the electrode is packed in a bag, the walls of which may be composed of any material or combination of materials which can impede to a substantially extent the permeation of gases from the inside of the bag to the outside as well as gases in the surrounding air to the inside of the bag.

A single material for the walls of the bag can generally not fulfil all the functions desired for the bag. Therefore, a laminate of several layers of material is generally used. Due to the properties of aluminium to impede permeation of oxygen, it is preferred to include a layer of aluminium or aluminium alloy in the laminate. Besides, the layer of aluminium or aluminium alloy, the laminate suitably comprises one or more films of a plastic material. The plastic material may be selected from the group consisting of low-density polyethylene, high-density polyethylene, polypropylene, and polyamide. Preferably, the layer of aluminium is provided with at least one layer of a plastic material on each side to avoid damage of the metallic layer.

The electrode according to the present invention may be used for a variety of applications, including monitoring, stimulation, therapeutical, and surgical purposes.

The monitoring applications include any measurement of the condition of the muscles or nerves of the human or animal body. Specific examples for the use of the electrode according to the present invention are ECG, EMG (electromyography) and EEG (electroencephalography).

The stimulation applications include any method for stimulation of the muscles or nerves of the human or animal body. Specific examples of the stimulation use of the electrode according to the present invention are defibrillation, pacing, and pain relief.

Examples of therapeutical applications of the electrode according to the present invention are electro therapy of muscles and nerves.

The electrode according to the present invention may also be used for surgical applications as grounding plate. A grounding plate is used in a certain surgical technique wherein the tissue of the patient is cut by a high-voltage needle. When the high-voltage needle is brought into contact with the skin, heat will develop and the tissue may be cut. The grounding plate is used to close the electrical circuit. To avoid burning, the grounding plate is usually provided with a fairly large skin contact area.

DETAILED DESCRIPTION OF THE FIGURES

Figure 1:
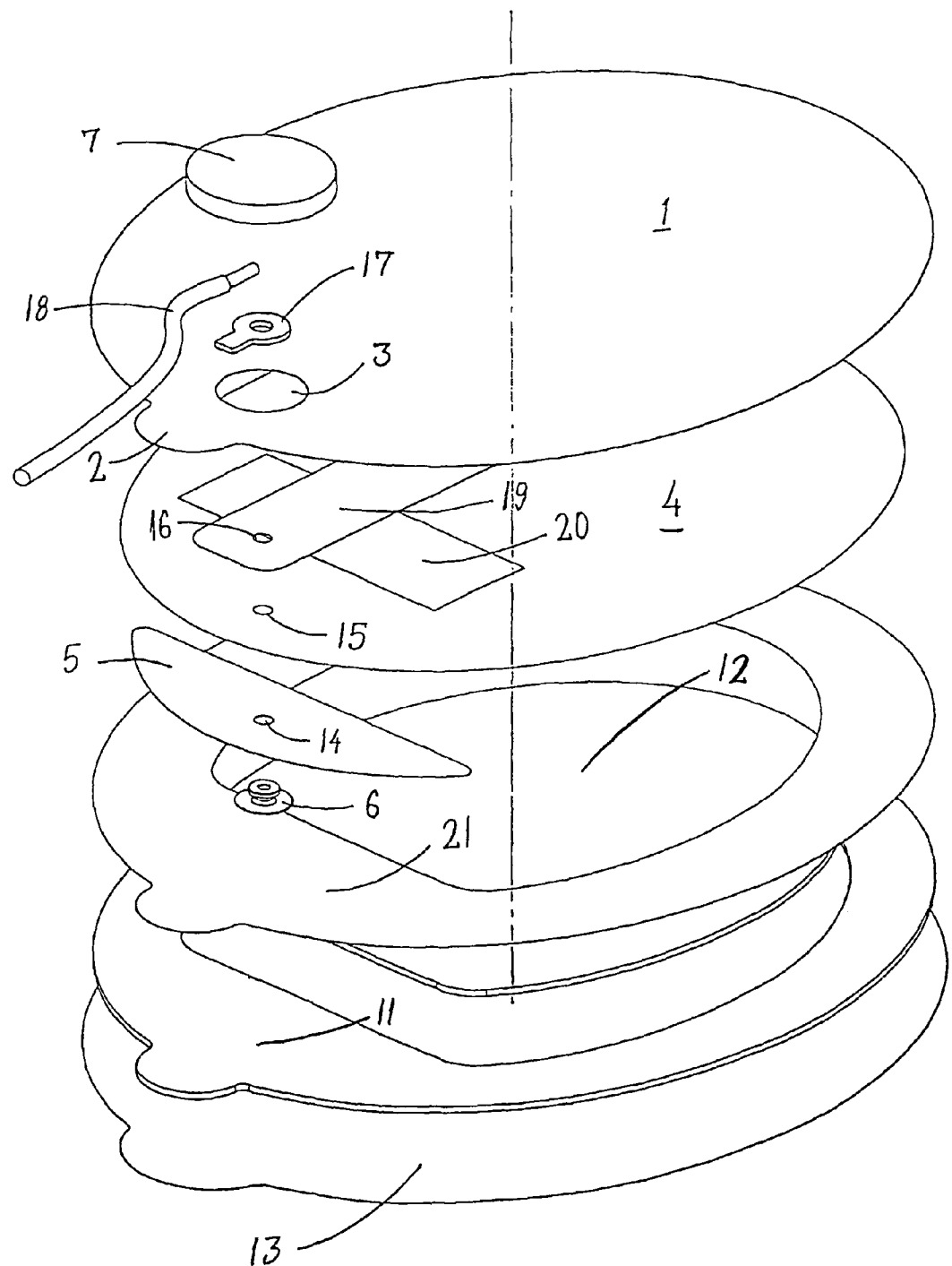
FIG. 1 shows an exploded view of an embodiment of the invention having a shield provided between the by-pass element and the electrically conductive layer.

FIG. 1 shows an exploded view of an electrode according to a preferred embodiment of the invention. The embodiment shown in FIG. 1 includes an electrically insulating backing or substrate 1. The substrate 1 has an oblong overall shape and an ear 2 attached to the circumference thereof. In addition, the substrate 1 comprises an aperture 3 near the ear 2. An electrically conductive layer 4 of tin foil is centred attached to the substrate 1. Between the substrate 1 and the electrically conductive layer 4, a by-pass element 19 is provided, and between the by-pass element and the electrically conductive layer, a shield 20 as aa adhesive tape is placed. On the face of the electrically conductive layer opposite the substrate, a relief film 5 is placed in the area in the vicinity of the point. A small hole 14 is provided in the relief film, and the electrically conductive layer 4 has a hole 15. Likewise, the by-pass element comprises a hole 16. Through the holes 14, 15, and 16, a rivet 6 is provided and meets the lug 17 to provide an effective electrical contact. A wire 18 is soldered to the lug 17, and a protective cap 7 is covering the electrically conductive parts.

A double sided adhesive tape 21 is provided at the perimeter area of the electrode and attaches a frame 11 to the electrically insulating backing. The area delimited by the frame 11 and a release liner 13 is filled with an electrically conductive gel 12.

Prior to the use of the skin electrode according to the embodiment shown in FIG. 1, the release liner is removed. Subsequently, the surface of the gel is brought into contact with the skin of a patient. The skin adhering ability of the gel ensures that the electrode remains in position.

Figure 2:
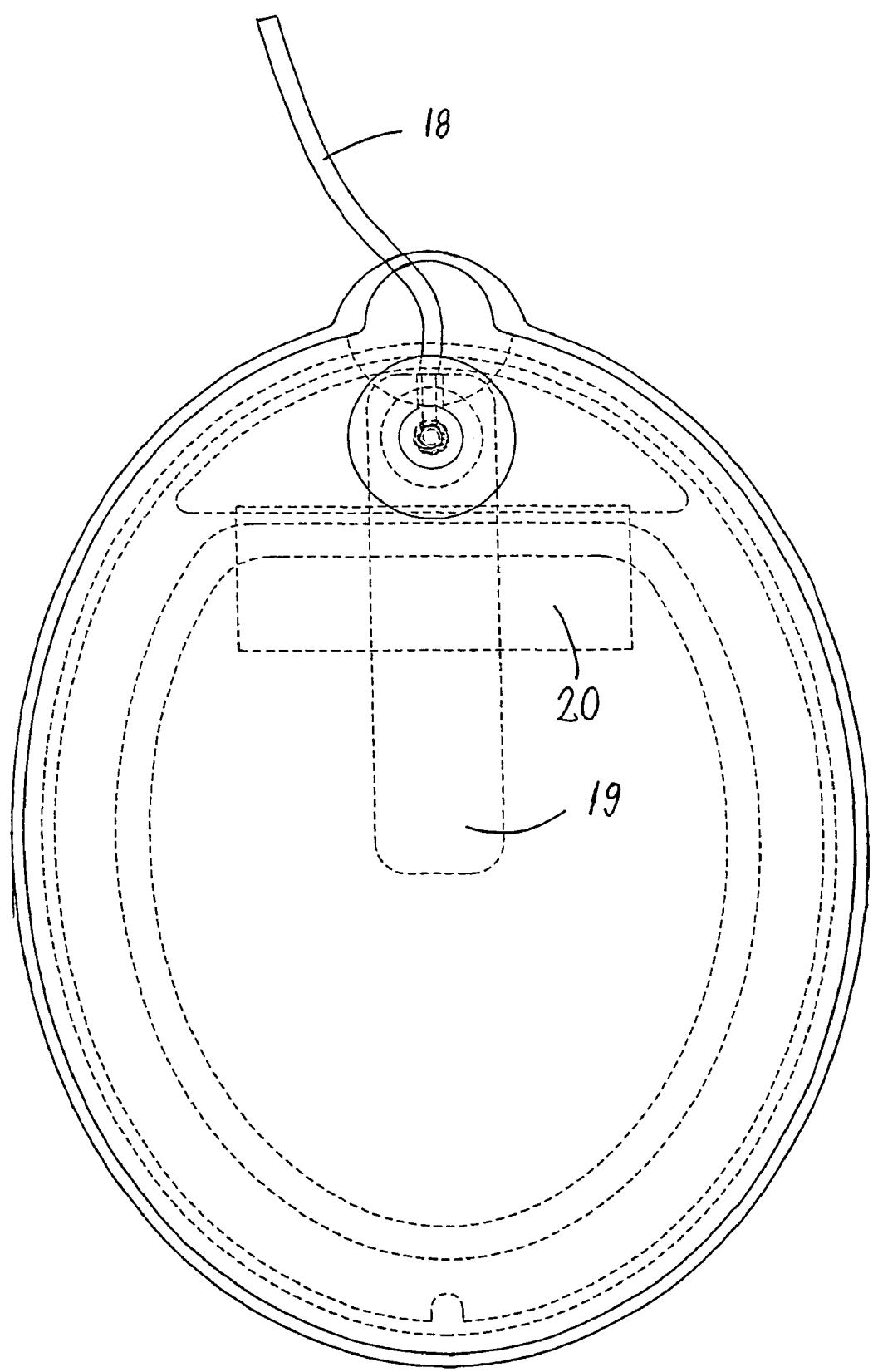
FIG. 2 shows a top view of the electrode shown in FIG. 1.

In FIG. 2, the by-pass element 19 of tin extents from the connection zone to a central area of the electrically conductive layer 4 of tin. At an area opposing the circumference of the electrically conductive gel closest to the connection zone, a shield 20 of a polymeric material is provided to prevent a possible pitting or etching of the electrically conductive layer 4 to protrude to the by-pass element 19.

The invention claimed is:

1. An electrode for establishing electrical contact with skin, comprising:
    an electrically conductive layer provided with means for establishing electrical connection to an apparatus for supplying or measuring electrical signals, and
    an electrically conductive gel covering a part of a first side of the electrically conductive layer so that the circumference of the electrically conductive gel at least partly crosses the surface of the first side of the electrically conductive layer,
    wherein an electrically conductive by-pass element provided with means for establishing electrical connection to said apparatus for supplying or measuring electrical signals, on the second side of the electrically conductive layer, is provided so that it extends over at least a part of said second side opposing the circumference of the gel crossing the surface of the electrically conductive layer on the first side and is in electrical contact with the second side of the electrically conductive layer at at least one point opposing an area covered with the electrically conductive gel at the first side of the electrically conductive layer.

2. An electrode according to claim 1, wherein a shield is provided between the by-pass element and an area of the second side of the electrically conductive layer opposing at least a part of the circumference of the electrically conductive gel on the first side.

3. An electrode according to claim 2, wherein the shield is of an insulating, flexible, polymeric material.

4. An electrode according to claim 3, wherein the shield is an adhesive tape.

5. An electrode according to claim 1, wherein the by-pass element and the electrically conductive layer share common means for connection to the apparatus for supplying or measuring electrical signals.

6. An electrode according to claim 1, wherein the electrically conductive layer and/or the by-pass element comprises a mixture of a binding agent and particles of a conducting material provided on a suitable carrier.

7. The electrode according to claim 6, wherein the particles of the conducting material is of carbon.

8. The electrode according to claim 6, wherein the particles of the conducting material is a mixture of particles of a metal and a salt of said metal.

9. The electrode according to claim 8, wherein the electrically conductive layer comprises Ag and AgCl particles distributed in the binding agent.

10. The electrode according to claim 6, wherein the carrier is an insulating, flexible, polymeric material.

11. The electrode according to claim 1, wherein the electrically conductive layer and/or the by-pass element comprises tin, aluminium, zinc, silver, lead or any combination thereof.

12. The electrode according to claim 1, wherein the pH of the electrically conductive gel is chosen so as to provide corrosion of the metal of the electrically conductive layer.

13. The electrode according to claim 1, wherein the electrically conductive gel is a hydrophilic polymer.

14. The electrode according to claim 13, wherein the hydrophilic polymer is selected from the group consisting of polyacrylate, polymethacrylate, polyacrylamide, poly(vinyl alcohol), poly(ethylene oxide), poly(ethylene imine), carboxymethylcellulose, methyl cellulose, poly(acryl amide sulphonic acid), polyacrylonitril, poly(vinylpyrrolidone), agar, dextran, dextrin, carrageenan, xanthan and guar.

15. The electrode according to claim 14, wherein the electrically conductive gel further comprises mineral or organic acids selected from the group consisting of hydrochloric acid, sulphuric acid, nitric acid, phosphorus acid, acetic acid, formic acid, benzoic acid, and sulfonic acid.

16. The electrode according to claim 14, wherein the electrically conductive gel further comprises an alkaline substance selected from the group consisting of ammonia, potassium hydroxide, sodium hydroxide, calcium hydroxide, pyridine, and aniline.

17. The electrode according to claim 14, wherein the electrically conductive gel further comprises an ionizable salt.

18. The electrode according to claim 14, wherein the ionizable salt is selected from the group consisting of KCl, KBr, NaCl, AgCl and $SnCl_2$.

19. An electrode according to claim 1, wherein the electrically conductive by-pass extends to a central area of the electrically conductive layer.

20. An electrode according to claim 1, wherein the by-pass element is covered with a conductive ink.

* * * * *